United States Patent [19]

Kanayama et al.

[11] Patent Number: 5,087,766
[45] Date of Patent: Feb. 11, 1992

[54] PROCESS FOR PRODUCING ALLYL-SUBSTITUTED PHENOL COMPOUND AND THE PRODUCT

[75] Inventors: Kaoru Kanayama; Shuji Ichikawa, both of Ibaraki, Japan

[73] Assignee: Mitsubishi Petrochemical Co., Ltd., Tokyo, Japan

[21] Appl. No.: 512,149

[22] Filed: Apr. 20, 1990

[30] Foreign Application Priority Data

Apr. 25, 1989 [JP] Japan ................................. 1-103446
Aug. 7, 1989 [JP] Japan ................................. 1-204080

[51] Int. Cl.$^5$ ............................................. C07C 39/12
[52] U.S. Cl. ................................... 568/718; 568/718; 568/720

[58] Field of Search ...................... 568/718, 719, 720

Primary Examiner—Werren B. Lone
Attorney, Agent, or Firm—Oblon, Spivak, McClelland, Maier & Neustadt

[57] ABSTRACT

A process for producing an allyl-substituted phenol compound is described, which comprises a combination of a first step in which a phenol is reacted with an allyl halide in the presence of an alkaline aqueous medium to allyl-etherify the phenol and a second step in which the reaction product obtained in the first step and containing the allyl-etherified phenol is subjected to a Claisen rearrangement reaction in the absence of a medium. Also, a compound obtained by the above process is described.

11 Claims, 2 Drawing Sheets

PROCESS FOR PRODUCING ALLYL-SUBSTITUTED PHENOL COMPOUND AND THE PRODUCT

FIELD OF THE INVENTION

The present invention relates to a process for producing an allyl-substituted phenol compound useful for imparting excellent heat resistance and excellent curability to encapsulants, laminates, fiber-reinforced composite materials, coating compositions, solder resists, adhesives, molding materials, pastes, and the like. More particularly, this invention relates to an industrially advantageous process for producing an allyl-substituted phenol compound from a phenol as a starting material in a high selectivity and yield with inhibited side reactions, and also relates to a compound obtained by the above process. Allyl-substituted phenol compounds are useful, for example, as intermediates for the synthesis of various fine chemicals and as hardeners for epoxy resins or maleimide resins.

BACKGROUND OF THE INVENTION

Allylphenols synthesized from phenols and allyl chloride and diallylbisphenols synthesized from bisphenols and allyl chloride have conventionally been known. Further, various resin compositions employing these allylphenols as hardeners have already been known such as, for example, a resin composition comprising an allylphenol and a maleimide compound (JP-A-55-39242), a resin composition comprising an allylphenol, a maleimide compound, and an epoxy resin (JP-A-53-134099), and a resin composition comprising an allylphenol, a maleimide compound, and a hydrazide. (The term "JP-A" as used herein means an "unexamined published Japanese patent application").

However, use of conventionally known allylphenols as hardeners for the above resins has been defective in that the compositions should be heated at high temperatures for long periods of time in order to complete crosslinking reactions and that crosslinked resins (cured products) produced are insufficient in heat resistance, flexibility, and impact resistance.

Known as the most common method for producing an allyl ether of a phenol is a process comprising dissolving a phenol in acetone, subsequently converting the phenol into a phenolate by use of an equimolar amount or a slight excess of potassium carbonate, and then reacting the phenolate with an equimolar amount of allyl bromide [*Journal of American Chemical Society*, Vol. 62, pp. 1863 (1940)]. The above reactions are completed by 5- to 10-hour stirring to give the intended allyl ether in a yield of 80 to 100%. Further, also known are a method that is the same as the above process except that allyl chloride or a combination of allyl chloride and sodium iodide is used in place of allyl bromide and a method that is the same as the above process except that sodium carbonate, sodium hydroxide, potassium hydroxide, sodium methoxide, sodium ethoxide, or the like is used in place of potassium carbonate. As the reaction medium for the above process, various organic polar solvents may be used besides acetone. Examples of such solvents include ketones such as methyl ethyl ketone and methyl propyl ketone (2-pentanone) and aliphatic alcohols such as methanol, ethanol, and n-propanol. (See, for example *Organic Reactions* (1944), Vol. II, pp. 22–28).

The above-described process for allyletherification employing a polar solvent such as those mentioned above, however, has been defective from the standpoint of industrial application because of the following disadvantages. Since inorganic salts (for example, NaCl, KCl, NaBr, KBr, etc.) formed as byproducts in the reactions generally are only slightly soluble in the polar solvent, the process necessitates a step of filtering off the inorganic salts after completion of the reactions. Moreover, in order to prevent the solution containing the allyl ether produced by the reactions from being emulsified when the ether is washed with pure water, the polar solvent, which is miscible with water, should be removed beforehand by evaporation and an only slightly water-soluble extraction solvent such as ether, benzene, toluene, ethyl acetate, methyl isobutyl ketone should be newly added. Furthermore, since the polar solvent is not so good in the ability to dissolve therein the base added and the phenolate generated, the process is not suited for industrial production in which the allyl ether is produced at a high concentration on a large scale.

Known as a method for producing an allyl-substituted phenol compound is a process in which an allyl ether of a phenol is subjected to an allyl-group rearrangement reaction, which is called the Claisen rearrangement, to produce a compound having an allyl-substituted aromatic nucleus. In this process, an allyl ether of a phenol is heated to isomerize the allyl ether to an o-allylphenol (a p-allylphenol if both ortho positions have a substituent). It has also been known that this rearrangement reaction generally proceeds easily by heating the allyl ether at a high temperature around 200° C. for several hours to several tens of hours in the presence or absence of a high boiling point solvent such as Carbitol, ethyl cellosolve, N,N-diethylaniline, N,N-dimethylaniline, tetralin, kerosene, and paraffin oil. (See, for example, *Organic Reaction* (1944), Vol. II, pp. 29–48).

However, because the rearrangement reaction is carried out at such a high temperature, allyl groups undergo heat polymerization and other side reactions to yield undesirable by-products, even though allyl group is far less apt to undergo polymerization than vinyl group, etc.

Although it has also been known that the rearrangement reaction is conducted under reduced pressure or in an atmosphere of carbon dioxide, nitrogen, etc., (see page 24 of the above-mentioned literature), the effect of suppressing side reactions has been insufficient.

In addition, although the use of a solvent of the above-mentioned kind, such as N,N-diethylaniline, tetralin, kerosene, and paraffin oil, serves to suppress polymerization reactions and improve selectivity and yield for obtaining the intended allylphenols (see page 24 of the above-mentioned literature), there are problems that such effects can generally be produced only when the solvent is used in a large quantity and that the solvent, especially diethylaniline, must be separated and removed after the rearrangement reaction by means of distillation or extraction with an aqueous solution of a mineral acid or by other means. Thus, the process employing a solvent is unsuited for industrial applications.

The Claisen rearrangement may be performed without such a high boiling point solvent, but this method has been defective in that because the reaction is carried out at a high concentration, intermolecular reactions are liable to proceed and, as a result, byproducts are formed by side reactions such as heat polymerization in large amounts as compared with the case employing a solvent.

On the other hand, as another method for the allylation of phenols, a process in which a phenol is allylated with an allyl halide in an aqueous medium is known (*J.A.C.S.*, 85, 1141 (1963)). In this process, in which a phenol or alkylphenol is reacted with an equimolar amount or less of an allyl halide, an aromatic-nucleus allylation reaction (C-allylation) takes place along with allyl-etherification (O-allylation) and the allylated product obtained is in the form of a mixture thereof. The allyl-substituted phenol obtained by this process also has a problem that where it is used as a hardener for a maleimide resin, the cure of the resin takes much time and the resulting cured products show insufficient performance.

SUMMARY OF THE INVENTION

The present inventors have conducted intensive studies in order to overcome the problems described above. As a result, it has now been found that the allylation reaction of a phenol with an allyl halide in an aqueous medium yields a product which is a mixture of an allyl ether that is the product of O-allylation of a phenolate, an allyl-substituted phenol formed from the keto-enol tautomer of a phenolate through C-allylation, and an O-allylated allyl-substituted phenol, the molecule of which has both C-allyl moiety and O-allyl moiety, and the content of the allyl-substituted phenol compound in these products is considerably high. It has also been found that the above reaction product readily undergoes the Claisen rearrangement to an allyl-substituted phenol compound at a high selectivity and a high conversion without side reactions such as polymerization, only when heated at a relatively low temperature in the absence of a medium. The present invention has been completed based on the above findings.

According to the first aspect of the present invention, a process for producing a high-purity allyl-substituted phenol compound is provided. The process of this invention comprises a combination of a first step in which a phenol is reacted with an allyl halide in the presence of an alkaline aqueous medium to allyl-etherify the phenol and a second step in which the reaction product obtained in the first step and containing the allyl-etherified phenol is subjected to a Claisen rearrangement reaction in the absence of a medium.

According to the second aspect of the present invention, a novel allyl-substituted phenol compound is provided which has more than one allyl group per aromatic ring and has excellent properties as a hardener for maleimide resins or other resins. The allyl-substituted phenol compound of this invention can be obtained by further reacting the reaction product obtained by the above-described process of this invention with an allyl halide, or by conducting the reaction of the first step of the above-described process of this invention by use of an allyl halide in an amount of 1.5 to 2.0 equivalent per aromatic ring of the phenol.

DETAILED DESCRIPTION OF THE INVENTION

Figure 1:
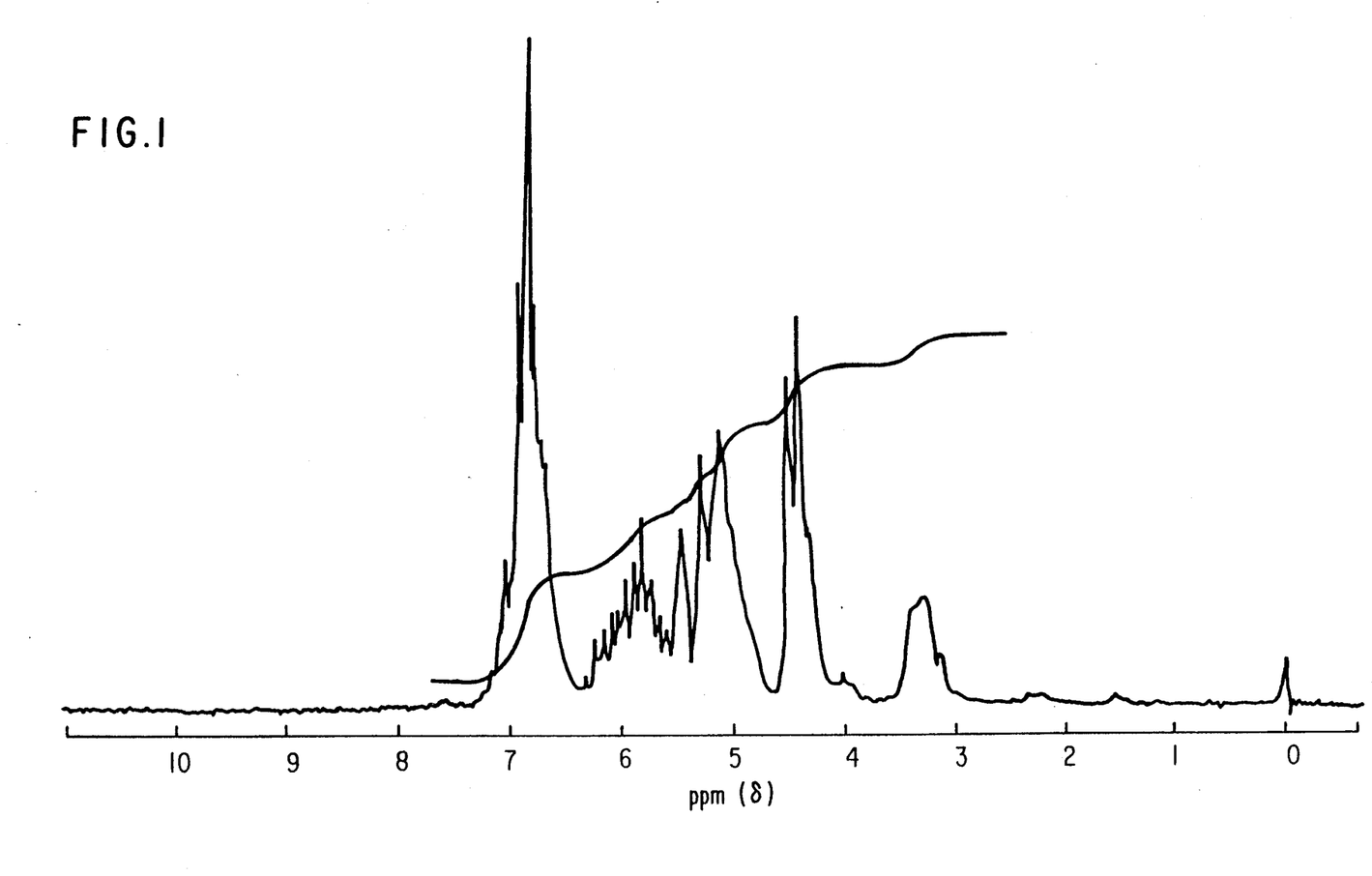
FIG. 1 shows the nuclear magnetic resonance spectrum of the polyallylated phenol compound obtained in Example 6.
Figure 2:
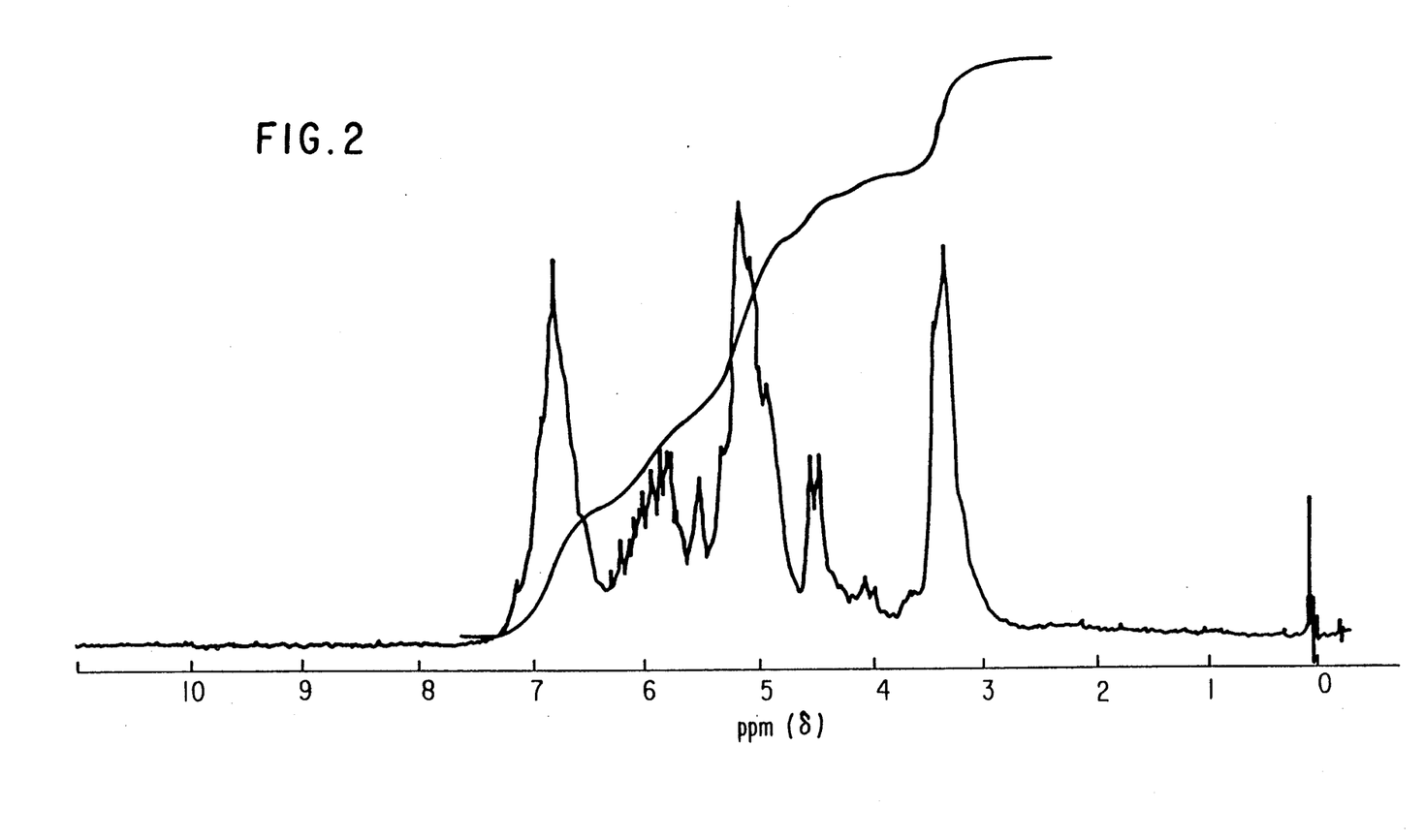
FIG. 2 shows the nuclear magnetic resonance spectrum of the polyallylated phenol compound obtained in Example 9.

The raw material phenol used in the process of this invention may be a phenol having a structure in which at least any one of the ortho positions and the para position based on the phenolic hydroxyl group is unsubstituted. Examples of such phenols include monohydric phenols such as phenol, o-cresol, m-cresol, p-cresol, o-chlorophenol, p-chlorophenol, o-nitrophenol, p-nitrophenol, p-aminophenol, o-methoxyphenol, p-methoxyphenol, p-acetoxyphenol, p-acetylphenol, 2,4-dimethylphenol, and 2,5-dimethylphenol; dihydric phenols such as catechol and hydroquinone, bis(hydroxyphenyl) compounds such as biphenol, 2,2-bis(4-hydroxyphenyl)-propane (i.e., bisphenol A), bis(4-hydroxyphenyl)methane (i.e., bisphenol F), 4,4'-dihydroxybenzophenone, 4,4'-dihydroxyphenyl sulfone, 3,9-bis(2-hydroxyphenyl)-2,4,8,10-tetraoxaspiro[5,5]undecane, 3,9-bis(4-hydroxyphenyl)2,4,8,10-tetraoxaspiro [5,5]undecane, and 1,1,1,3,3,3-hexafluoro-2,2-bis(p-hydroxyphenyl)-propane (i.e., hexafluorobisphenol A); and polyphenols such as phenolic novolak, cresolic novolak, a polyphenol obtained by reacting salicylaldehyde with phenol or cresol in the presence of an acid catalyst, a polyphenol obtained by reacting p-hydroxybenzaldehyde with phenol or cresol in the presence of an acid catalyst, and a polyphenol obtained by reacting terephthalaldehyde with phenol, cresol or bromophenol in the presence of an acid catalyst.

Preferred of those are poly(hydroxyphenyl) compounds. Particularly preferred are bisphenol A and a polyphenol represented by the following formula (II):

wherein n is an integer of 1 to 10.

The process for producing an allyl-substituted phenol compound according to the first aspect of this invention comprises a combination of a first step in which a phenol is allyl-etherified and a second step in which the reaction product obtained in the first step and containing the allyl-etherified phenol is subjected to a Claisen rearrangement reaction in the absence of a medium. In the allyl-etherification of the first step, a phenol is reacted with an allyl halide in the presence of a base, such as an alkali metal hydroxide, and an aqueous medium. This reaction yields a reaction product that is a mixture of an allyl ether and an allyl-substituted phenol. (If allylation is conducted in an organic solvent, the allylation reaction is one-hundred-percent allyl-etherification (O-allylation), and allylation of aromatic nuclei (C-allylation) does not occur). Although the content of the allyl-substituted phenol in the reaction product is not constant and varies depending on the structure of the raw phenol, the content is normally in the range of from 10 to 45% by weight based on the amount of the reaction product (i.e., the total amount of the allyl ether of the phenol and the allyl-subsituted phenol).

As the allyl halide used in the above reaction, allyl chloride and allyl bromide are normally employed. Of these, allyl chloride is preferred mainly from the economical standpoint.

As the base used in the above reaction, an alkali metal hydroxide is preferred, such as sodium hydroxide, potassium hydroxide, etc. However, alkali metal carbonates such as sodium carbonate and potassium carbonate and alkali metal alcoholates of aliphatic alcohols such as sodium methoxide and sodium ethoxide may be used. Because carbonates require much time to form phenolates and alkali metal alcoholates are costly, alkali metal hydroxides are preferred.

The aqueous medium used as the medium for the above reaction may be ion-exchanged water or distilled water, and may also be tap water or well water because they have almost no effect on the selectivity and yield of the product (allyl-substituted phenol compound). However, if an allyl-substituted phenol compound having an ionic impurity content of several ppm or less is to be produced, ion-exchanged water is preferred.

In the above reaction, both of the introduced amount of the allyl halide and that of the base are preferably in the range of from 1.0 to 1.5 equivalent per hydroxyl group of the phenol. Furthermore, it is preferable that the molar amount of the allyl halide (except allyl chloride) be the same as that of the base, because such amounts make the reaction product solution neutral. If the amounts of the allyl halide and the base introduced are less than 1.0 equivalent, the reaction cannot proceed sufficiently. If the molar amount of the base is larger than that of the allyl halide, allyl alcohol results as a by-product and the reaction cannot proceed sufficiently in this case as well. However, only where allyl chloride is used as the allyl halide, it is preferable that allyl chloride be introduced in an amount 1.1 to 1.3 times the amount of the base because allyl chloride has a low boiling point (i.e., volatile).

The first step of the process of this invention is explained below in detail, with a case where an alkali metal hydroxide is used as the base being taken as an example. First, an alkali metal hydroxide is dissolved in water, and a predetermined amount of a phenol is added to this solution. Upon stirring at room temperature, the phenol dissolves in the solution normally in about 1 to 10 minutes to give an aqueous phenolate solution. It is preferred to adjust the phenolate concentration in the water to 0.2 to 10 mol/l. If the phenolate concentration is less than 0.2 mol/l, productivity is impaired. If the concentration thereof exceeds 10 mol/l, complete dissolution of the phenolate cannot be attained depending on the kind of the phenolate and it takes much time to complete the reaction.

In the case where a polyphenol represented by the formula (II) given above is used as the phenol, it is preferred to adjust the concentration of the polyphenol (II) to 10 to 70% by weight based on the amount of the water. If the concentration of the polyphenol (II) exceeds 70% by weight, part of the polyphenol is present in an undissolved state and it disadvantageously takes much time to complete the reaction. On the other hand, a concentration thereof less than 10% by weight is uneconomical although the reaction proceeds smoothly.

Subsequently, a predetermined amount of an allyl halide is added to the above-obtained aqueous phenolate solution over a period of 5 to 20 minutes, and a reaction is allowed to proceed by heating the resulting reaction mixture at 40° to 100° C., preferably 60° to 80° C., for 0.5 to 6 hours, preferably 2 to 4 hours, with stirring. If the reaction temperature is less than 40° C., it takes much time to complete the reaction, while if it exceeds 100° C., bumping of the reaction solution is apt to occur. The reaction time varies depending on the kind of the phenol, but is normally about 2 to 4 hours when the reaction temperature is in the above range. In the case where allyl chloride is used as the allyl halide, since allyl chloride has a low boiling point (45° C.), it is preferable that the reaction be first conducted by stirring the reaction mixture at a temperature of about 40° C. for 1 to 2 hours to thereby allow an allyl-etherification reaction to proceed to some degree, and then the reaction be conducted further at a heightened temperature of 60° to 80° C. for 2 to 3 hours. Thus, the reaction can be performed efficiently while bumping is being prevented. In carrying out the reaction of the first step, it is preferred to accelerate the reaction by stirring the reaction system at 100 to 300 rpm, because the allyl ether produced is insoluble with water, so that the reaction solution becomes turbid and unhomogeneous as the reaction proceeds, and because the allyl halide is only slightly soluble in the reaction solution in the beginning of the reaction.

After completion of the reaction of the first step, a proper extraction solvent is added to the resulting reaction solution in an amount ⅓ to 2 times by volume the amount of the whole reaction solution, and extraction treatment is conducted by stirring the resulting mixture for 5 to 30 minutes. Upon this extraction treatment, the reaction solution separates into two layers, i.e., an aqueous layer containing an inorganic salt (sodium chloride, sodium bromide, etc.) and an organic layer containing the reaction product.

As the extraction solvent, a water-insoluble organic solvent is used such as, for example, benzene, toluene, ethyl acetate, methyl isobutyl ketone, diethyl ether, petroleum ether, petroleum benzene, methylene chloride, chloroform, carbon tetrachloride, and chlorobenzene. In view of the generally employed reaction vessel of the type in which the contents are withdrawn from a lower part thereof, a solvent which gives an organic layer positioned over an aqueous layer is preferred. Examples of such preferred solvents include benzene, toluene, ethyl acetate, methyl isobutyl ketone, diethyl ether, petroleum ether, and petroleum benzene. Of these, solvents in which reaction products including an allyl-etherified phenol are easily soluble, such as, for example, toluene, ethyl acetate, methyl isobutyl ketone, and diethyl ether, are particularly preferred.

In conducting the reaction of the first step of the process of this invention, an organic solvent such as those mentioned above may be added along with the aqueous medium. In this case, the reaction proceeds in a two-layer system and the allyl-etherified phenol formed in the aqueous layer moves to the organic layer, with the equilibrium state in the aqueous layer being broken, and as a result, the amount of the allyl-substituted phenol compound in the reaction product is decreased and the amount of the allyl ether is increased. In such a case where the reaction is performed by use of an organic solvent along with the aqueous medium, a phase-transfer catalyst such as tetrabutylammonium fluoride, phenyltrimethylammonium fluoride, or tetraethylammonium fluoride may be added in an amount of 1 to 5% by weight based on the amount of the phenol. By addition of such phase-transfer catalyst, reaction efficiency can be heightened.

After completion of the above-described reaction of the first step according to this invention, which is conducted in the presence of an aqueous medium and in the presence or absence of an organic solvent, the resulting organic layer is separated from the aqueous layer as described above, and washed two or five times with 0.5- to 3-fold volume of distilled water or ion-exchanged water, and then the organic solvent is removed by evaporation, thereby to obtain a reaction product (a mixture of an allyl ether and an allyl-substituted phenol) of the first step. The yield in the first step (the yield of the total of the allyl-etherified phenol and the allyl-substituted phenol based on the raw phenol) is 85 to 100%.

In the second step of the process of this invention, the reaction product obtained in the first step and containing the allyl-etherified phenol is subjected to a Claisen rearrangement reaction in the absence of a medium. This Claisen rearrangement reaction is carried out by heating the reaction product at a proper temperature. The heating temperature and heating time vary to some extent depending on the kind (reactivity) of the phenol and cannot be specified indiscriminately. However, the heating is performed generally at a temperature of 150° to 190° C. for 1 to 10 hours, preferably at 175° to 185° C. for 3 to 8 hours. The reaction pressure is not particularly limited and the reaction may be conducted under reduced pressure, or ordinary pressure, or increased pressure. Further, the atmosphere of the reaction system may be air or may be inert gas such as nitrogen or carbon dioxide gas.

The allyl-substituted phenol compound which is the desired product in the second step of the process is obtained in a conversion and yield almost as high as 100% based on the amount of the reaction product of the first step (the total of the allyl ether of the phenol and the allyl-substituted phenol).

In this case, an allylated product having any C-allylation degree in the range of from 30 to 100% can be obtained by ceasing the rearrangement reaction in the course thereof. In the case where a polyphenol represented by the formula (II) given above has been used as the phenol and the rearrangement reaction is carried out at 180° C. in the absence of a medium, 37% of the O-allylated product is converted to a C-allylated product in 1 hour, 61% in 2 hours, 79% in 3 hours, and almost 100% in 4 hours.

In practicing the whole first and second step of the process of this invention, use may be made of a generally employed reactor equipped, for example, with a stirrer, a heater that can regulate temperature up to around 200° C., a device for measuring internal temperature, a heat exchanger (condenser), an evacuating device, a feed opening for an allyl halide, etc., and a valve for withdrawing the contents from the lower part of the reactor. Only one reactor of such a type suffices to carry out the whole procedures of the process, and by use of such a reactor, a high-purity allyl-substituted phenol compound can easily be produced in a high conversion and high yield.

According to the second aspect of this invention, a novel allyl-substituted phenol compound is provided which has allyl groups in an amount more than one equivalent per aromatic nucleus of the phenol moiety, and which can be obtained by the following methods.

One method for obtaining the allyl-substituted phenol compound is to utilize the above-described process of this invention. The one-hundred-percent C-allylated product obtained by the above-described process of this invention is used as a raw material to conduct reallylation, whereby two allyl groups are incorporated into one aromatic nucleus. In this case also, the O-allylation/C-allylation ratio can be varied by controlling the Claisen rearrangement. By repeating the same reaction, an allyl-substituted phenol compound in which three allyl groups have been incorporated into one aromatic nucleus can be obtained.

Although it is economically advantageous to perform the reallylation in an aqueous alkali solution, the reallylation may also be conducted in an organic solvent (for example, an alkali-dissolving solvent such as propanol, butanol, etc.). In this case, one-hundred-percent O-allylation occurs.

Another method for obtaining the allyl-substituted phenol compound is to carry out the reactions of the above-described process of this invention with the alkali and the allyl chloride being used in the first step in excess amounts, i.e., both in the range of from 1.5 to 2.0 equivalent, whereby 1.3 allyl groups are incorporated on the average. The O-allyl/C-allyl ratio can be likewise varied by controlling the Claisen rearrangement.

In this case also, further allylation can be performed. The number of allyl groups incorporated varies depending on the percentage of C-allylation, but it is possible to incorporate 2.3 to 2.6 allyl groups.

For example, in the case where a polyphenol represented by formula (II) given hereinbefore is used as the phenol, an allyl-substituted phenol compound represented by the following formula (I) is obtained.

wherein $R^1$, $R^2$ and $R^3$ independently represent hydrogen atom or $-CH_2-CH=CH_2$, p, q, and r independently are 0, 1 or 2, and n is an integer of 1 to 10, provided that $2(2n+1) \geq n(q+r)+p \geq 2n+1$ and in the case of $n(q+r)+p=2n+1$, any one of $R^1$, $R^2$ and $R^3$ is not hydrogen atom.

By blending the allyl-substituted phenol compound of this invention with a polymaleimide compound having at least two maleimide groups per molecule in such proportions that allyl group/maleimide group = 1.0/0.1 to 1.0/10.0 (in terms of equivalent), and heat-curing the resulting blend, a cured product having excellent heat resistance is obtained. In general, as the number of allyl group becomes large, heat resistance is improved but there is a tendency for the cured product to show a slightly decreased strength. Further, a high percentage of C-allylation results in a high strength, while a high percentage of O-allylation results in improvements in moisture resistance, heat resistance, and curability.

Therefore, by practicing the present invention, a heat-resistant resin with desired performance is easily obtained. Normally, the composition is cured at a temperature of generally 150° to 300° C., preferably 175° to 250° C., for generally 0.5 to 24 hours, preferably 1 to 5 hours. An accelerator such as a tertiary amine, a quarternary ammonium salt, a Lewis acid salt such as BF$_3$, or a peroxide may effectively be incorporated, according to need, in an amount of 0.1 to 2.0 parts by weight per 100 parts by weight of the resin composition.

Examples of polymaleimides that can be used with the allyl-substituted phenol compound of this invention include the following:

(i) bismaleimides such as N,N'-ethylenebismaleimide, N,N'-hexamethylenebismaleimide, N,N'-m-phenylenebismaleimide, N,N'-p-phenylenebismaleimide, N,N'-4,4'-diphenylmethanebismaleimide, N,N'-3,3'-dimethyl-5,5'-diethyl-diphenylmethanebismaleimide, N,N'-(4,4'-diphenylether)bismaleimide, N,N'-methylenebis(3-chloro-p-phenylene)bismaleimide, N,N'-(4,4'-diphenyl sulfone)bismaleimide, N,N'-4,4'-dicyclohexylmethanebismaleimide, N,N'α,α'-4,4'-dimethylenecyclohexanebismaleimide, N,N'-m-xylenebismaleimide, N,N'-4,4'-diphenylcyclohexanebismaleimide, N,N'-4,4'-triphenyl-1,1-propanebismaleimide, N,N'-4,4'-triphenyl-1,1,1-ethanebismaleimide, N,N'-4,4'-triphenylmethanebismaleimide, N,N'-3,5-triazole-1,2,4-bismaleimide, 2,2-bis[4-(4-maleimidophenoxy)phenyl]-propane, and bis[4-(4-maleimidophenoxy)phenyl]sulfone;

(ii) a poly(N-phenylmethylene)maleimide represented by the following general formula wherein n is a number of 0 to 4; and

(iii) a polymaleimide represented by the following general formula (see JP-A-59-12931)

-continued and a mixture comprising the above polymaleimide and a polymaleimide represented by the following general formula (see JP-A-60-26032)

wherein X represents hydrogen atom, a halogen atom, or an alkyl or alkoxy group having 1 to 4 carbon atoms and m is 0 or an integer of 1 to 4.

The present invention will be explained below in more detail by reference to the following Examples and Comparative Examples.

EXAMPLE 1

(Synthesis of Polyphenol)

Into a 1-liter three-necked flask equipped with a thermometer, stirrer, and condenser were introduced 470 g of phenol, 61 g of salicylaldehyde, and 0.1 g of sulfuric acid. The temperature in the flask was raised to 110° C. and then held at that temperature for 4 hours, thereby allowing a reaction to proceed. After completion of the reaction, the reaction mixture was transferred to a separatory funnel, diluted with 500 ml of methyl isobutyl ketone (hereinafter, abbreviated as "MIBK"), and then washed three times with 300 ml of distilled water to remove the sulfuric acid. The resulting solution was transferred to a rotary evaporator, and the MIBK and an excess of the phenol were removed by evaporation under reduced pressure, thereby obtaining a reddish-brown glass-like polyphenol represented by formula (II). This polyphenol had a melting point of 111° C. and an average molecular weight of 353.

(Synthesis of Allyl-Substituted Phenol)

Into a 2-liter four-necked flask made of glass and equipped with a stirrer, thermometer, condenser, and dropping funnel were introduced aqueous sodium hydroxide solution (obtained by dissolving 102 g of sodium hydroxide in 1 liter of water) and 280 g of the polyphenol synthesized above. The resulting mixture was stirred at room temperature for 15 minutes to obtain a solution of a phenolate of the polyphenol. To this solution, 244 g of allyl chloride was then added dropwise from a dropping funnel over a period of 10 minutes. The resulting mixture was heated to 45° C. on an oil bath, stirred for 1 hour, subsequently heated to 65° C., and then stirred for 2.5 hours, thereby allowing a reaction to proceed. After completion of the reaction, the reaction mixture was cooled to 45° C. and 700 ml of toluene was added thereto. This mixture was stirred for 10 minutes. The resulting reaction solution, which had separated into two layers, was transferred to a separatory funnel and the lower aqueous layer was separated and removed. The organic layer was washed three times with 500 ml of distilled water and then the toluene was completely removed therefrom by evaporation under reduced pressure, thereby obtaining 831 g of a reddish-brown viscous reaction product. Upon analysis by nuclear magnetic resonance spectroscopy and gel permeation chromatography, this reaction product was found to be a mixture of 68% by weight of a product of O-allylation of the polyphenol and 32% by weight of a C-allylation product. It was also found from $^1$H-NMR analysis that the reaction product as a whole had 1.03 allyl groups per aromatic nucleus.

The above-obtained reaction product was transferred to a 500-ml separable flask, heated to 180° C. with stirring on an oil bath, and then kept at that temperature for 4.5 hours, thereby conducting a Claisen rearrangement reaction. As a result, 380 g of a reddish-brown semisolid product was obtained. Upon analysis by nuclear magnetic resonance spectroscopy and gel permeation chromatography, this product was found to be an allyl-substituted polyphenol (average molecular weight 413, viscosity 25.6 poises, conversion 100%, selectivity 99%) containing no ally ether remaining unrearranged, with 1% by weight of products of side reactions.

COMPARATIVE EXAMPLE 1

(Allyl-Etherification)

Into a 1-liter four-necked flask equipped with a stirrer, thermometer, condenser, and dropping funnel were introduced 700 ml of n-propyl alcohol and 41.3 g of sodium hydroxide. The resulting mixture was stirred until it became uniform. Thereto was then added 100 g of the polyphenol synthesized in Example 1, and the resulting mixture was stirred for 1 hour. Subsequently, 87.8 g of allyl chloride was added dropwise to the above mixture over a period of 10 minutes. The reaction solution was then heated to 100° C. and stirred for 3 hours, thereby allowing a reaction to proceed. The reaction product was filtered to remove common salt formed as a by-product, and then the n-propyl alcohol was removed by evaporation under reduced pressure and recovered, thereby obtaining 125 g of a reddish-brown viscous liquid reaction product. Upon analysis by nuclear magnetic resonance spectroscopy and gel permeation chromatography, this reaction product was found to be an allyl ether of the polyphenol.

(Claisen Rearrangement)

The allyl-etherified polyphenol obtained above was heated to 180° C. on an oil bath in the same manner as in Example 1 and kept at that temperature for 4.5 hours, 6 hours, or 7 hours, thereby conducting a Claisen rearrangement reaction for each time period. As a result of the analysis of each product, the product of the 4.5-hour rearrangement reaction was found to be a mixture of 70% by weight of a C-allylated product and 28% by weight of the allyl ether remaining unrearranged (conversion 71%, selectivity 98%) with 2% by weight of by-products, the product of the 6-hour rearrangement reaction was found to be a mixture of 85.5% by weight of a C-allylated product and 12% by weight of the allyl ether remaining unrearranged (conversion 88%, selectivity 97.5%) with 2.5% by weight of by-products, the product of the 7-hour rearrangement reaction was found to be a mixture of 96% by weight of a C-allylated product and 1.5% by weight of the allyl ether remaining unrearranged (conversion 98%, selectivity 97.5%).

COMPARATIVE EXAMPLE 2

In 200 ml of Carbitol was dissolved 130 g of the allyl-etherified polyphenol synthesized in Comparative Example 1. This solution was heated to 195° C. on an oil bath and kept at that temperature for 4.5 hours to conduct a Claisen rearrangement reaction. The resulting product was analyzed in the same manner as in Example 1 and, as a result, it was found to be a mixture of 73% by weight of a C-allylated product and 24% by weight of the allyl ether remaining unrearranged (conversion 75%, selectivity 97%) with 3% by weight of by-products.

EXAMPLE 2

(Synthesis of Polyphenol)

Into a 2-liter four-necked flask equipped with a thermometer, stirrer and condenser, were introduced 1.8 kg of phenol, 161 g of terephthalaldehyde, and 4.9 g of 4N-hydrochloric acid. The resulting mixture was heated to 100° C. and allowed to react at that temperature for 2 hours. After completion of the reaction, the reaction mixture was transferred to a separatory funnel, where the mixture was diluted with 500 ml of MIBK and then washed, three times with 300 ml of distilled water to remove the hydrochloric acid. The resulting reaction solution was transferred to a rotary evaporator and the MIBK and an excess of the phenol were removed by evaporation under reduced pressure, thereby obtaining a reddish-brown glass-like polyphenol. This polyphenol had a softening point of 127° to 132° C. and an average molecular weight of 610.

(Synthesis of Allyl-Substituted Polyphenol)

In the same reactor as that used in Example 1 were placed an aqueous alkali solution (obtained by dissolving 132 g of sodium hydroxide in 1.0 liter of water) and then 300 g of the polyphenol obtained above. This mixture was subjected to an allylation reaction in the same manner as in Example 1 except that the amount of allyl chloride added was 253 g, and then the reaction mixture was post-treated and the resulting product was analyzed, in the same manner as in Example 1. As a result, the reaction product was found to be a mixture of 79% by weight of a product of O-allylation of the polyphenol and 21% by weight of a C-allylation product. The reaction product as a whole had 1.05 allyl groups per aromatic nucleus.

The above-obtained reaction product (415 g) was then transferred to a 500-ml separable flask, heated to 180° C. with stirring on an oil bath, and then kept at that temperature for 4 hours, thereby conducting a Claisen rearrangement reaction. As a result, 415 g of a reddish-brown glass-like solid product was obtained. This product was analyzed in the same manner as in Example 1, and was found to be an allyl-substituted polyphenol (average molecular weight 780, softening point 66°–70°

C., conversion 100%, selectivity 98.5%) containing no allyl ether remaining unarranged.

EXAMPLE 3

(Synthesis of Allyl-Substituted Phenol)

Into the same reactor as that used in Example 1 were introduced aqueous sodium hydroxide solution (obtained by dissolving 77 g of sodium hydroxide in 1 liter of water) and then 277 g of 3,9-bis(2-hydroxyphenyl)-2,4,8,10-tetraoxaspiro[5,5]undecane (which had been synthesized by reacting 2-hydroxybenzaldehyde with pentaerythritol in the presence of an acid catalyst) as a dihydric phenol. This mixture was subjected to an allylation reaction in the same manner as in Example 1 except that the amount of allyl chloride added was 160 g, and then the reaction mixture was post-treated and the resulting product was analyzed, in the same manner as in Example 1. As a result, the reaction product was found to be a mixture of 75% by weight of a product of O-allylation of the dihydric phenol and 25% by weight of a product of C-allylation of the dihydric phenol. The reaction product as a whole had 1.02 allyl groups per aromatic nucleus.

(Claisen Rearrangement)

The above-obtained reaction product (318 g) was transferred to a 500-ml separable flask, heated to 180° C. with stirring on an oil bath, and then kept at that temperature for 8 hours, thereby conducting a Claisen rearrangement reaction. As a result, 316 g of a reddish-brown semisolid product was obtained. This product was analyzed in the same manner as in Example 1, and was found to consist of a product of diallyl substitution of the dihydric phenol (yield from the dihydric phenol 93%, viscosity at 30° C. 41 poises, conversion 100%, selectivity 98%) and contain no diallyl-etherified product.

EXAMPLE 4

(Synthesis of Allyl-Substituted Phenol)

Into the same reactor as that used in Example 1 were introduced aqueous sodium hydroxide solution (obtained by dissolving 156 g of sodium hydroxide in 1 liter of water) and then 279 g of biphenol. This mixture was subjected to an allylation reaction in the same manner as in Example 1 except that the amount of allyl chloride added was 256 g, and then the reaction mixture was post-treated and the resulting product was analyzed, in the same manner as in Example 1. As a result, the reaction product was found to be a mixture of 67% by weight of a product of O-allylation and 33% by weight of a product of C-allylation. The reaction product as a whole had 1.03 allyl groups per aromatic nucleus.

The above-obtained product (387 g) was transferred to a 500-ml separable flask, heated to 180° C. with stirring on an oil bath, and then kept at that temperature for 4 hours, thereby conducting a Claisen rearrangement reaction. As a result, 387 g of a white crystalline product was obtained. This product was analyzed in the same manner as in Example 1, and was found to be a mixture containing 1% by weight of biphenol diallyl ether remaining unrearranged and 98% by weight of diallylbiphenol (conversion 99%, selectivity 99%).

EXAMPLE 5

(Synthesis of Allyl-Substituted Phenol)

Into a 500-liter reaction vessel equipped with a stirrer, a heater capable of regulating temperature up to 200° C., a device for measuring internal temperature, a heat exchanger (cooling device), an evacuating device, a feed opening for feeding materials from the upper part of the vessel, and a valve for withdrawing the contents from the lower part of the vessel were introduced 21 kg of sodium hydroxide and 200 liters of well water. This mixture was stirred at 150 rpm for 10 minutes to give aqueous sodium hydroxide solution. To this solution was added 50 kg of the polyphenol synthesized in Example 1. The resulting mixture was heated to 35° C. and stirred at 260 rpm for 1 hour, and then the polyphenol was ascertained to have been dissoloved completely.

While the above-obtained solution was kept being stirred at 260 rpm at an internal temperature of 35° C., 45.1 kg of allyl chloride was added to the solution over a period of 20 minutes. The stirring was continued for 1 hour, and then the resulting mixture was heated to 75° C. over a period of 1 hour and stirred at that temperature for 2 hours to complete the reaction. The reaction solution was cooled to 50.5° C., 45 kg of toluene and 50 kg of MIBK were added thereto, and the resulting mixture was then stirred at 150 rpm for 15 minutes. After the resulting reaction mixture was allowed to stand for 15 minutes, the lower valve was opened to withdraw the resulting aqueous layer, which weighed 224 kg, as the lower layer. Subsequently, 100 kg of ion-exchanged water was added to the organic layer remaining in the vessel, and the resulting mixture was stirred at 50 rpm for 10 minutes and then allowed to stand for 15 minutes. The resulting aqueous layer was withdrawn from the bottom. This washing procedure was repeated four times, and the resulting organic layer was heated under reduced pressure to completely remove the toluene and MIBK by evaporation. A slight amount was taken out of the thus-obtained product and analyzed. As a result, this product was found to be a mixture of 69% by weight of an allyl ether of the polyphenol and 31% by weight of an allyl-substituted polyphenol.

The above-obtained product was heated to 180° C., and then stirred at 100 rpm under reduced pressure (9 mmHg) for 4.5 hours, thereby conducting a Claisen rearrangement reaction. Thereafter, the reaction mixture was cooled to 130° C. under ordinary pressure and then 62.6 kg of a reddish-brown semisolid product was withdrawn through the lower valve. This product was analyzed in the same manner as in Example 1 and, as a result, it was found to be an allyl-substituted polyphenol (average molecular weight 413, viscosity 25.6 poises, conversion 100%, selectivity 99.5%) containing no allyl ether remaining unrearranged.

As apparent from the above Examples, by the process according to the first aspect of this invention, an allyl-substituted phenol compound can be produced in a high yield with high conversion and selectivity, while side reactions, particularly polymerization reactions, are being suppressed.

EXAMPLE 6

Into a 2-liter four-necked separable flask made of glass and equipped with a stirrer, thermometer, condenser, and dropping funnel were introduced aqueous sodium hydroxide solution (obtained by dissolving 320 g (8 moles) of sodium hydroxide in 1 liter of water) and 400 g (4 equivalent) of the polyphenol obtained in Example 1 (Synthesis of polyphenol). The resulting mixture was stirred at ordinary temperature for several minutes to obtain a homogeneous phenolate solution. To this solution, 612 g (8 moles) of allylchloride was added dropwise from the dropping funnel over a period of 10 minutes. After 1-hour stirring, the resulting mixture was heated to 50° C. on an oil bath, stirred for 1 hour, subsequently heated to 60° C., and then stirred for 2 hours, thereby allowing a reaction to proceed. After completion of the reaction, the reaction mixture was cooled to ordinary temperature. The resulting reaction solution, which had separated into two layers, was transferred to a separatory funnel and the lower aqueous layer was separated and removed. Subsequently, 1 liter of MIBK was added to the organic layer and the resulting mixture was washed five times with 1 liter of distilled water. The MIBK and allyl chloride remaining unreacted were removed under reduced pressure from the resulting reaction mixture and recovered, thereby obtaining 575 g of a reddish-brown viscous reaction product (viscosity 27 poises, average molecular weight 471). Upon analysis by nuclear magnetic resonance spectroscopy, this product was found to have 1.3 allyl groups per aromatic ring with O-allyl 66% by weight and C-allyl 34% by weight.

EXAMPLE 7

Into a 300-ml three-necked flask equipped with a stirrer, thermometer, and condenser was introduced 200 g of the polyallylated product obtained in Example 6. This polyallylated product was heated to 180° C. on an oil bath and then stirred for 3 hours to conduct a Claisen rearrangement reaction. The thus-obtained polyallylated product was a reddish-brown viscous liquid. Upon NMR analysis, the percentage of C-allylation was found to be 80% by weight.

EXAMPLE 8

The same procedures as in Example 7 were repeated except that the Claisen rearrangement reaction was performed for 4.5 hours. As a result, the polyallylated product obtained had a C-allylation percentage of 100% by weight.

EXAMPLE 9

Into the same reactor as that used in Example 1 were introduced 1.1 liter of aqueous sodium hydroxide solution (obtained by dissolving 102 g (2.55 moles) of sodium hydroxide in 1 liter of water) and 280 g (2.8 equivalent) of the polyphenol obtained in Example 1. This mixture was subjected to the same treatments as those in Example 1 except that 244 g (3.2 moles) of allyl chloride was added dropwise, thereby obtaining 381 g of a reddish-brown viscous substance. This substance was transferred to a 500-ml separable flask, heated with stirring to 180° C. on an oil bath, and then kept at that temperature for 4.5 hours to conduct a Claisen rearrangement reaction. Thus, 380 g of a 100% C-allylated product was obtained as a reddish-brown semisolid.

The above-obtained product was placed in the reactor again and dissolved in 1.3 liter of aqueous sodium hydroxide solution (2 mol/l). To this solution was added 93.3 g (1.22 mole) of allyl chloride. The resulting mixture was heated to 45° C. on an oil bath, stirred for 1 hour, subsequently heated to 65° C., and then stirred for 2.5 hours, thereby conducting a reaction. After completion of the reaction, the reaction mixture was cooled to ordinary temperature and 900 ml of MIBK was added thereto. This mixture was stirred for 10 minutes. The resulting reaction solution, which had separated into two layers, was transferred to a separatory funnel and the lower aqueous layer was removed. Subsequently, the organic layer was washed three times with 800 ml of distilled water. The MIBK was removed from the resulting reaction mixture under reduced pressure and recovered, thereby obtaining 332 g of a reddish-brown viscous product (viscosity 103 poises, average molecular weight 521).

Upon NMR analysis, the above obtained product was found to have 1.4 allyl groups per aromatic ring, with O-allyl 28% by weight and C-allyl 72% by weight.

APPLICATION EXAMPLE 1

68.5 Grams (0.6 equivalent) of the allylated polyphenol produced in Example 6, 88 g (0.5 equivalent) of diaminodiphenylmethanebismaleimide (Polymaleimide A; MB-3000; produced by Mitsubishi Petrochemical Co., Ltd., Japan), and 365 g of fused silica were kneaded with each other for 10 minutes by means of 6-inch rolls heated to 95° C. to 105° C. The resulting composition was pulverized to obtain a molding powder. This powder was examined for gelation time at 200° C. The powder obtained above was shaped by means of a press heated at 200° C., and this shape was then postcured at 250° C. for 5 hours to obtain a strong cured product. Properties of the cured product thus obtained are summarized in Table 1.

APPLICATION EXAMPLES 2 TO 8

The same procedures as in Application Example 1 were repeated except that the formulations shown in Table 1 were used, thereby obtaining cured products. Properties of these products are also shown in Table 1.

COMPARATIVE APPLICATION EXAMPLE 1

107 Grams (0.7 equivalent) of O,O'-diallylbisphenol A, 125 g (0.7 equivalent) of diaminodiphenylmethanebismaleimide (Polymaleimide A; MB 3000; produced by Mitsubishi Petrochemical Co., Ltd.), and 479 g of fused silica were formed into a molding powder in the same manner as in Application Example 1. This powder was shaped by means of a press heated at 200° C. and the shape was then postcured at 250° C. for 5 hours. Properties of the thus-obtained cured product are also shown in Table 1.

COMPARATIVE APPLICATION EXAMPLE 2

The same procedure as in Application Example 1 was repeated except that the formulation shown in Table 1 was used. The result obtained is also shown in Table 1.

APPLICATION EXAMPLE 9

In a round-bottom flask were placed 51 g (0.45 equivalent) of the allylated product produced in Example 6 and 80g (0.45 equivalent) of diaminodiphenylmethanebismaleimide (Polymaleimide A). The resulting mixture was heated to 150° to 180° C. on an oil bath to melt the mixture. This melt was degassed under reduced pressure, poured into a mold preheated at 150° C., and then heated at 180° C. for 2 hours in the first stage and then at 250° C. for 5 hours in the second stage. The thus-cured composition was cooled slowly, thereby obtaining an excellent cast-molded article. Properties of this article are summarised in Table 2.

APPLICATION EXAMPLES 10 TO 15

The same procedures as in Application Example 9 were repeated except that the formulations shown in Table 2 were used, thereby obtaining cast-molded articles. Properties of the articles are also shown in Table 2.

COMPARATIVE APPLICATION EXAMPLE 3

From 129 g of O,O'-diallylbisphenol A and 150 g of diaminodiphenylmethanebismaleimide (Polymaleimide A), a cast-molded article was obtained in the same manner as in Application Example 9. Properties of this article are also shown in Table 2.

In Tables 1 and 2, polymaleimides and poly-allylated compounds are referred to as the following.

(1) Polymaleimide A; diaminodiphenylmethanebismaleimide (MB-3000, manufactured by Mitsubishi Petrochemical Co., Ltd.).

(2) Polymaleimide B; polymaleimide (MP-2000X, manufactured by Mitsubishi Petrochemical Co., Ltd.) produced from terephthalaldehyde, aniline, o-toluidine, and maleic anhydride.

(3) Polyallylated compound A; O,O'-diallylbisphenol A.

(4) Polyallylated compound B; diallyl ether of bisphenol A.

TABLE 1

|  | Application Example | | | | | | | | Comparative Application Example | |
|---|---|---|---|---|---|---|---|---|---|---|
|  | 1 | 2 | 3 | 4 | 5 | 6 | 7 | 8 | 1 | 2 |
| Formulation (parts) | | | | | | | | | | |
| Polymaleimide | | | | | | | | | | |
| A (1) | 100 | 100 | 100 | 70 | 100 | 70 | 100 | 100 | 100 | 100 |
| B (2) | — | — | — | 30 | — | 30 | — | — | — | — |
| Polyallylated Compound | | | | | | | | | | |
| Kind | Ex. 1 | Ex. 6 | Ex. 6 | Ex. 6 | Ex. 9 | Ex. 9 | Ex. 7 | Ex. 8 | A (3) | B (4) |
| Amount | 78 | 78 | 64 | 55 | 100 | 94 | 64 | 64 | 86 | 86 |
| Fused silica | 415 | 415 | 383 | 362 | 467 | 453 | 383 | 383 | 434 | 434 |
| Gelation time (min) @ 200° C. | 8 | 7.5 | 7 | 7 | 8 | 7 | 4 | 2 | 25 | 65 |
| Property of cured product | | | | | | | | | | |
| Glass transition temperature (°C.) (Tg)[1] | 345 | 380 | 376 | 383 | 371 | 375 | 379 | 376 | 291 | Unable to be shaped at 200° C. |
| Linear expansion coefficient ($\times 10^{-5}$/°C.) ($\alpha_1$)[2] | 1.4 | 1.32 | 1.27 | 1.25 | 1.26 | 1.24 | 1.27 | 1.27 | 1.59 | Unable to be shaped at 200° C. |
| Flexural strength[3] (kg/mm$^2$) @ 260° C. | 4.4 | 4.6 | 4.8 | 5.0 | 4.1 | 4.3 | 4.9 | 4.9 | 3.6 | Unable to be shaped at 200° C. |
| Water absorption[4] (%) | 1.25 | 1.20 | 1.22 | 1.26 | 1.18 | 1.20 | 1.20 | 1.15 | 1.30 | |

[1]Measured by means of Thermal Mechanical Analysis, using Rigaku Thermoflex TMA 8140 (manufactured by Rigaku Co. Ltd.) at the rising rate of temperature of 2° C./min in nitrogen stream.
[2]Measured at temperatures not higher than Tg under the conditions of [1].
[3]JIS K-6911
[4]121° C., 100% RH, 100 hrs.

TABLE 2

|  | Application Example | | | | | | | Comparative Application Example |
|---|---|---|---|---|---|---|---|---|
|  | 9 | 10 | 11 | 12 | 13 | 14 | 15 | 3 |
| Formulation (parts) | | | | | | | | |
| Polymaleimide | | | | | | | | |
| A (1) | 100 | 100 | 100 | 70 | 100 | 100 | 100 | 100 |
| B (2) | — | — | — | 30 | — | — | — | — |
| Polyallylated Compound | | | | | | | | |
| Kind | Ex. 6 | Ex. 6 | Ex. 6 | Ex. 6 | Ex. 9 | Ex. 9 | Ex. 7 | A (3) |
| Amount | 64 | 48 | 85 | 55 | 100 | 50 | 64 | 86 |
| Property of cured product | | | | | | | | |
| Glass transition temperature (°C.) (Tg)[1] | 386 | 391 | 382 | 390 | 390 | 388 | 381 | 293 |
| Linear expansion coefficient ($\times 10^{-5}$/°C.) ($\alpha_1$)[2] | 3.56 | 3.84 | 4.16 | 3.53 | 3.61 | 3.78 | 3.88 | 4.35 |
| Flexural strength[3] (kg/mm$^2$) @ 260° C. | 4.1 | 4.0 | 4.0 | 4.3 | 3.8 | 4.0 | 5.5 | 3.1 |
| Heat deformation temperature[4] (°C.) | 364 | 368 | 365 | 371 | 368 | 370 | 362 | 305 |
| 5% Weight less temperature (°C.)[5] | 437 | 444 | 439 | 443 | 441 | 447 | 442 | 338 |

[1]Measured by means of Thermal Mechanical Analysis, using Rigaku Thermoflex TMA 8140 (manufactured by Rigaku Co., Ltd.) at the rising rate of temperature of 2° C./min in nitrogen stream.
[2]Measured at temperatures not higher than Tg under the conditions of [1].
[3]JIS K-6911
[4]ASTM D-648
[5]Measured by means of Thermal Gravitynetive Analysis, using SFC-580 (manufactured by Seiko I & E Co., Ltd.) at the rising rate of temperature of 10° C./min.

While the invention has been described in detail and with reference to specific embodiments thereof, it will be apparent to one skilled in the art that various changes and modifications can be made therein without departing from the spirit and scope thereof.

What is claimed is:

1. A process for producing an allyl-substituted phenol compound, comprising the steps of:

reacting a phenol, in which at least one of the ortho-positions and para-position based on the phenolic hydroxyl group of said phenol is unsubstituted, with an allyl chloride or allyl bromide in the presence of an alkaline aqueous medium at a temperature and for a reaction time sufficient to allyl-etherify said phenol; and then rearranging said allyl-etherified phenol at a temperature and for a time sufficient to rearrange said allyl-etherified phenol by Claisen rearrangement in the absence of a reaction medium.

2. A process as claimed in claim 1, wherein the allyl halide is used in an amount of 1.0 to 1.5 equivalent per hydroxyl group of the phenol.

3. A process as claimed in claim 1, wherein the allyl-etherification is carried out at 40° to 100° C.

4. A process as claimed in claim 1, wherein the Claisen rearrangement is carried out at 150° to 190° C.

5. A process as claimed in claim 1, wherein the phenol is a poly(hydroxyphenyl) compound.

6. An allyl-substituted phenol compound obtained by a process comprising a combination of a first step in which a poly(hydroxyphenyl) compound is reacted with an allyl halide in the presence of an alkaline aqueous medium to allyl-etherify the phenol and a second step in which the reaction product obtained in the first step and containing the allyl-etherified phenol is subjected to a Claisen rearrangement reaction in the absence of a medium.

7. An allyl-substituted phenol compound as claimed in claim 6, wherein the poly(hydroxyphenyl) compound is a polyphenol represented by the following formula (II)

wherein n is an integer of 1 to 10.

8. A process for producing an allyl-substituted phenol compound, which comprises a combination of a first step in which a phenol is reacted with an allyl halide in the presence of an alkaline aqueous medium to allyl-etherify the phenol, a second step in which the reaction product obtained in the first step and containing the allyl-etherified phenol is subjected to a Claisen rearrangement reaction in the absence of a medium, and a third step in which the allyl-substituted phenol compound obtained in the second step is reacted with an allyl halide.

9. A process as claimed in claim 8, wherein the third step is carried out in the presence of an alkaline aqueous medium or an organic solvent.

10. A process for producing an allyl-substituted phenol compound, which comprises reacting a phenol with an allyl halide in the presence of an alkaline aqueous medium to allyl-etherify the phenol, said allyl halide being used in an amount of 1.5 to 2.0 equivalent per hydroxyl group of the phenol.

11. A process as claimed in claim 10, wherein the phenol is a polyphenol represented by the following formula (II)

wherein n is an integer of 1 to 10.

* * * * *